(12) United States Patent
Ehrhard et al.

(10) Patent No.: US 6,395,289 B1
(45) Date of Patent: *May 28, 2002

(54) HYDROPHILIC POLYMER BLENDS USED TO PREVENT COW SKIN INFECTIONS

(75) Inventors: Joseph Ehrhard, Flemington; Michael Eknoian, Newark; Alfredo Vinci, Lawrenceville, all of NJ (US)

(73) Assignee: Hydromer, Inc., Branchburg, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/557,716

(22) Filed: Apr. 25, 2000

Related U.S. Application Data

(63) Continuation-in-part of application No. 09/106,680, filed on Jun. 29, 1998, now Pat. No. 6,203,812.

(51) Int. Cl.$^7$ .............................................. A01N 25/24
(52) U.S. Cl. ................. 424/407; 424/78.25; 424/78.35; 424/78.03; 424/78.05; 424/78.06; 424/78.07; 424/78.24; 424/59; 424/63; 424/401; 424/405; 424/406; 424/486; 424/487; 424/672; 424/744; 424/DIG. 10; 424/DIG. 13; 424/438; 424/667; 514/458; 514/635; 514/738; 514/919; 523/122
(58) Field of Search ................................. 424/407, 405, 424/406, 78.03, 78.08, 78.07, 78.24, 438, 401, 78.25, 78.35, 59, 63, 486, 487, 667, 672, DIG. 13, DIG. 10, 744; 523/122; 514/919, 738, 458, 635

(56) References Cited

U.S. PATENT DOCUMENTS

| | | |
|---|---|---|
| 3,728,449 A | 4/1973 | Cantor et al. |
| 3,993,777 A | 11/1976 | Caughman et al. |
| 4,049,830 A | 9/1977 | Pugliese |
| 4,113,854 A | 9/1978 | Andrews et al. |
| 4,199,564 A | 4/1980 | Silver et al. |
| 4,258,056 A | 3/1981 | Lentsch |
| 4,311,709 A | 1/1982 | Dybas et al. |
| 4,376,787 A | 3/1983 | Lentsch et al. |
| 4,446,153 A | 5/1984 | Yang |
| 4,542,012 A | 9/1985 | Dell ........................... 424/28 |
| 4,642,267 A | 2/1987 | Creasy et al. |
| 5,017,369 A | 5/1991 | Marhevka |
| 5,503,838 A | 4/1996 | Schmidt et al. |
| 5,529,770 A | 6/1996 | McKinzie ................. 424/78.2 |
| 5,641,498 A | 6/1997 | Loosemore |
| 6,203,812 B1 * | 3/2001 | Ehrhard et al. ............. 424/407 |

FOREIGN PATENT DOCUMENTS

| | | |
|---|---|---|
| CA | 1 065 254 | 10/1979 |
| EP | 0 473 026 A1 | 3/1992 |
| WO | WO 98/04136 | 2/1998 |

\* cited by examiner

*Primary Examiner*—Neil S. Levy
(74) *Attorney, Agent, or Firm*—Hoffmann & Baron, LLP

(57) ABSTRACT

The invention discloses a mammalian teat dip for controlling mastitis, a method for preparing the composition and a method of treatment of mammals. The composition contains a film-forming polymer blend, at least one antimicrobial and a sodium bicarbonate buffering agent. The polymer blend contains a solvent-soluble, thermoplastic polyurethane and a hydrophilic poly(N-vinyl lactam). Upon application to mammalian skin, this composition leaves a long-lasting, water-resistant, residual, elastic film that treats and protects mammalian skin from infection.

23 Claims, No Drawings

HYDROPHILIC POLYMER BLENDS USED TO PREVENT COW SKIN INFECTIONS

This application continuation-in-part of Ser. No. 09/106,680 filed on Jun. 29, 1998, Now U.S. Pat. No. 6,203,812 pending. The entire disclosure of the aforementioned prior application is incorporated herein by reference.

BACKGROUND OF THE INVENTION

The effective management and maintenance of large dairy herds and the production of dairy products has been a major agricultural accomplishment. One of the problems in maintaining large herds is the health of the individual animals. One health problem that causes significant economic problems relates to mastitis. Often during milking, the skin of the dairy animal is irritated by automatic milking machines. This irritation, characterized by redness and occasionally by areas of broken skin, can be the site of a microbial attack causing mastitis. Animals that contract mastitis must be removed from service resulting in the loss of the dairy output. As a result, a significant amount of attention has been focused on preventing the development of mastitis or treating mastitis in dairy herds.

The dairy farmer is faced with two different types of mastitis infections. Contagious mastitis is spread during the milking process through contact between the animal and dairy equipment that may carry a source of a mastitis pathogen. Contagious mastitis is most easily controlled by using germicidal post milking teat dips. Such germicidal dips kill bacteria that are introduced onto the surface of the animal from the milking machines. The second type of mastitis, environmental mastitis, is caused by contamination of the animal surface by materials from the barn yard environment, fields, barn interior, etc. Such pathogens include *E. coli, Streptococcus uberis, klebsiella* and others. Such contamination occurs as the animal moves through its environment. Environmental mastitis is best treated with a barrier film that protects sensitive tissues from contamination.

In the treatment and prevention of mastitis the use of Protective coatings, formed from aqueous coating systems, has been an option for many years. One class of coating compositions is characterized by being actively antimicrobial. These coatings prevent the incidence of infection in the animal through the presence of an active biocide. Another class of coating materials is characterized by the formation of film barriers on the skin surface to prevent contact between vulnerable tissues and the environment. Many antimicrobial materials are incompatible with a variety of these polymeric or film forming materials. Recent product developments provide coatings for teat skin which form film barriers, as well as, contain antimicrobial agents.

In the typical operations of a dairy herd, the herd is brought into a milking station and the udder is washed to remove the barrier film. Any delay in removal of the film can substantially reduce productivity and substantially increase time required to deal with a large herd. Further, difficulty in removing the film can cause abrasion or bruising to the animal which can promote mastitis. Therefore, it is important that the films are easily removed in less than 15 minutes, preferably in less than 10 minutes, using water or mild cleaning solutions. In the periods between milking, the animal is released into the environment to graze. While grazing the animal is exposed to environmental water from dew, mud, rain and ponds. This exposure to water can cause the barrier film to rub off.

Among the materials used in barrier-type or film-type teat dips are solubilized liquids, polyvinylpyrrolidone and other vinyl polymers, protein hydrozylate, natural and synthetic gums, water, ethanol, methanol, isopropanol, soluble polymers, unsaturated fatty oils, cellulose derivatives, acrylic polymer lattices, etc.

Latex provides an effective covering of teat skin which can be combined with an antimicrobial agent (U.S. Pat. No. 4,113,854). However, the latex material has the serious drawback of not being readily removable when the next milking time arrives. The result can be a partially-removed coating, leaving behind particles which become trapped in the milk line filters. The difficulties of removal can also result in excessive rubbing of the teat skin, thus leading to irritation. Furthermore the use of latex can potentially result in milk contamination.

On the other hand, teat dips which are easy to remove, for example, polyvinyl alcohol based teat dips, do not provide adequate water resistance. Such films do not remain on a dairy animal for the duration between milking periods. Due to exposure to water, these films wear off in about 3 to 4 hours. Without an adequate barrier film the dairy animal is vulnerable to environmental pathogens which will promote mastitis in the herd.

The following disclosures have been identified as part of the technology of the related art. Typical disclosures of disinfectant after-milking teat dips (aimed at destroying any pathogens remaining on the teats after milking) can be found in British Patent 1 144 637 (Kelco Chemicals, Ltd.), published on Mar. 5, 1969; Meave et al., J. Dairy Science, 52:6696 (1969); Dodd et al., 'Mastitis Control,' Biennial Reviews (1970) University of Redding, England, National Institute of Research of Dairying, pp. 21–57; Lentsch, U.S. Pat. No. 4,258,056; Lentsch et al., U.S. Pat. No. 4,376,787; Yang, U.S. Pat. No. 4,446,153; Marhevka, U.S. Pat. No. 5,017,369; Cantor et al., U.S. Pat. No. 3,728,449; Pankey, 'Postmilking Teat Antisepsis,' Symposium on Bovine Mastitis, Veterinary Clinics of North America: Large Animal Practice, Vol. 6, No. 2, July 1984; Pankey et al., 'Efficacy Evaluation of Two New Teat Dip Formulations Under Experimental Challenge,' Journal Dairy Science, 68:462–465 (1985), Philpot et al., 'Hygiene in the Prevention of Udder Infections. V. Efficacy of Teat Dips Under Experimental Exposure to Mastitis Pathogens,' Journal Dairy Science, 61:956–963 (1978), Bennett, 'Teat Dip as a Component of Coliform Mastitis Control, Dairy and Food Sanitation,' Vol. 2, No. 3, pp. 110–114 (March 1982), Eberhart et al, 'Germicidal Teat Dip in a Herd with Low Prevalence of Streptococcus agalactiae and Staphylococcus aureau Mastitis,' Journal Dairy Science, 66:1390–1395 (1983).

Typical disclosures of protective or barrier-type teat dips be found in Loosemore et al., U.S. Pat. No. 5,641,498, Schmidt et al., U.S. Pat. No. 5,503,338, Acres et al., U.S. Pat. No. 3,066,071, Krause, U.S. Pat. No. 3,222,252, Philpot et al., Journal Dairy Science, 58:205–216, Coughman et al., U.S. Pat. No. 3,993,777, Pugliese, U.S. Pat. No. 4,049,830, Silver et al., U.S. Pat. No. 4,199,564, Dybas et al., U.S. Pat. No. 4,311,709 and Andrews et al., U.S. Pat. No. 4, 113,854. Still also for examples of such materials, see Farnsworth, Journal of American Veterinary Medical Association, 177:441 (1980) and Farnsworth et al., The Bovine Practitioner, No. 16, pp. 28–29 (1981). Still further, please review Canadian Patent No. 1,065,254 and European Published Application No. 25,640 (Mar. 25, 1981).

A substantial need exists for an antimicrobial and barrier teat dip that can be easily and rapidly removed during milking operations while imparting sustained water resistance between milking periods.

SUMMARY OF THE INVENTION

The present invention is a new mammalian teat dip composition as well as a method for treating mammalian skin. This film-forming composition exhibits antimicrobial properties against the typical contagious mastitis causing pathogens and barrier properties protecting the animal from environmental mastitis.

This aqueous based composition includes a solution of a water-resistant, film forming, polymer blend, at least one antimicrobial agent and sodium bicarbonate to bring the pH of the composition to approximately 4 to 6.5. Examples of antimicrobial agents include iodine, chlorhexidene, bronopol and triclosan. Upon application to a substrate, this composition leaves a long-lasting, water-resistant, residual, elastic film which treats and protects mammalian skin from infection.

In one formulation the iodine-containing antimicrobial agent is added as an aqueous solution of polyvinylpyrrolidone-iodine (PVP-$I_2$). In another formulation the iodine-containing antimicrobial agent is added as an aqueous solution of elemental iodine and iodide salts. In yet another formulation the iodine-containing antimicrobial agent is added as an aqueous solution of elemental iodine, hydriodic acid, and a surfactant. The surfactant can range widely in its degree of ionization, including no ionization.

The chlorhexidine-containing antimicrobial agent can be added as an aqueous solution of chlorhexidine salts.

The polymer blend, as taught by U.S. Pat. No. 4,642,267 (Hydromer, Inc.), consists essentially of two polymer components. One polymer component is an organic, solvent-soluble, preformed, thermoplastic polyurethane which has no reactive isocyanate groups. The other polymer component is a hydrophilic poly(N-vinyl lactam). This polymer blend is capable of withstanding exposure to water without a significant loss of the hydrophilic poly(N-vinyl lactam).

The polyurethane of the polymer blend can be derived from an aromatic polyisocyanate and a polyether polyol; or from an aliphatic polyisocyanate and a polyether polyol; or from an aromatic polyisocyanate and a polyester polyol; or from an aliphatic polyisocyanate and a polyester polyol.

The poly(N-vinyl lactam) of the polymer blend is a water-soluble polyvinylpyrrolidone homopolymer or a poly(N-vinyl caprolactam) homopolymer.

The polymer blend may contain at least one additional compatible polymer component. The additional polymer component is a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

The composition may also contain water-soluble or water-dispersible skin conditioning agents, such as glycerin; glycols; polyols, such as polyethylene glycol; lanolin; aloe vera and vitamins. The composition may also contain colorants, fragrances and insect repellants.

The present invention also provides a method of protecting a mammalian teat from infection. This method includes applying the composition to the mammalian teat and evaporating the solvent portion of the composition to form a protective water resistant film.

The instant composition in addition to protecting the animal from contamination and allowing easy removabilty prior to milking, provides an increased resistance to premature loss. Thus, when an animal is released into the environment, the composition will be resistant to environmental water, remaining on the animal for the period between milkings. Unlike polyvinyl alcohol-based formulations which wear off in about 3 to 4 hours, the instant invention imparts water resistance up to 8 hours. Moreover, when the animal returns to the milking site, the antimicrobial barrier coating can be easily removed in about 5 minutes using an aqueous wash. Milking can continue without delay and after milking is finished, the animal can again be treated with the aqueous material forming a new antimicrobial barrier film.

DETAILED DESCRIPTION

The aqueous compositions and the resulting films of this invention provide barrier layers containing antimicrobial agents which prevent the contact between the animal skin and microorganisms either from the environment or from other animals. These films provide extended water resistance without compromising the ease of removability necessary to run a productive dairy operation. This invention also discloses a method of protecting mammalian teat skin from infection.

The novel aqeous mammalian teat dip composition includes a solution of a water-resistant, film-forming polymer blend, at least one antimicrobial agent and sodium bicarbonate. The composition contains an amount of the polymer sufficient to form a water-resistant film upon topical application.

The antimicrobial agent is present in the composition in an amount which is sufficient to protect mammalian skin from infection by typical contagious and environmental mastitis-causing pathogens and/or treat the mammalian skin. Protecting mammalian skin from infection includes the reduction of the incidence of infection. Treating the mammalian skin includes the reduction of the inflammation and/or infection of the skin. A sufficient amount of antimicrobial would be an amount that would reduce the incidence of infection or reduce the inflammation and/or infection once it has occurred. Upon application to a substrate, this composition forms a water-resistant, residual, elastic film.

The sodium bicarbonate is present in an amount to provide the resulting teat dip composition with a pH of approximately 4 to 6.5; most preferably to a pH of approximately 5.5. A teat dip composition with the preferred sodium bicarbonate concentration and the preferred pH has a typical iodine color.

The composition can include, for example, 50% to 95% by weight of water; 0.01% to 2.0% by weight of a thickener; 0.1% to 20% by weight of a water-resistant, film forming, polymer blend; up to 10% by weight of an aqueous acid; up to 5% by weight of sodium bicarbonate and about 0.05% to 5% by weight of an antimicrobial agent. Examples of antimicrobial agents are iodine, chlorhexidene, bronopol and triclosan. The composition may also include 0.05% to 10% of one or more water-soluble or water-dispersible skin conditioning agents.

One preferred antimicrobial agent of the invention is an aqueous solution of iodine (AST, Inc.). A formulation of this aqueous solution contains 50% to 98.9% by weight of water, 0.1% to 49% by weight of elemental iodine, and 1% to 49.9% % by weight of iodide salts. Another formulation of this aqueous solution contains 50% to 97.9% by weight of water, 0.1% to 48% % weight of elemental iodine, 1% to 48.9% by weight of hydriodic acid, and 1% to 48.9% by weight of a surfactant. The surfactant can be cationic, anionic, non-ionic or any combination of these. Iodine can also be added as a powder of polyvinylpyrrolidone-iodine (PVP-$I_2$). The aqueous solution formed from PVP-$I_2$ powder contains 50% to 80% by weight of water and 20% to 50% % by weight of PVP-$I_2$.

Another preferred antimicrobial agent of the invention is chlorhexidine. Chlorhexidine may be added as an aqueous solution which includes 50% to 99% water and 0.1% to 50% chlorhexidine salts.

The polymer blend used in the instant invention is taught by U.S. Pat. No. 4,642,267 (Hydromer, Inc.). It consists of essentially two polymer components. One polymer component is an organic, solvent-soluble, preformed, thermoplastic polyurethane having no reactive isocyanate groups. The other polymer component is a hydrophilic poly(N-vinyl lactam). This polymer blend is capable of withstanding exposure to water without significant loss of the hydrophilic poly(N-vinyl lactam).

The polyurethane of the polymer blend can be derived from an aromatic polyisocyanate and a polyether polyol; or from an aliphatic polyisocyanate and a polyether polyol; or from an aromatic polyisocyanate and a polyester polyol; or from an aliphatic polyisocyanate and a polyester polyol.

The poly(N-vinyl. lactam) of the polymer blend is a water-soluble polyvinylpyrrolidone homopolymer or a poly (N-vinyl caprolactam) homopolymer.

The polymer blend may contain at least one additional compatible polymer component. An additional compatible polymer component is one which does not interfere with the barrier properties, hydrophilic/hydrophobic balance and easy removability of the composition. The additional polymer component is a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

These blends exhibit properties intermediate those of the polyurethane component and those of the poly(N-vinyl lactam) component. Blends which are predominantly made up of the hydrophilic poly(N-vinyl lactam) component readily absorb water to become soft and slippery. Blends which are predominantly made up of the polyurethane component are relatively hard but still wettable. Exhibiting properties intermediate of those of polyurethane and poly (N-vinyl lactam) enables the dual characteristic of the present invention. Though capable of being removed easily, the present invention provides sustained water resistance.

Exposure of the claimed compositions to water, even for prolonged periods, does not result in any significant loss of the hydrophilic poly(N-vinyl lactam) component, possibly as a result of associative forces with the polyurethane component, chain entanglement, or both. Whatever may, in fact, be the basis for this property, this property contributes to the ability of the composition to remain on dairy animals despite prolonged contact with environmental water. There is no significant loss of the composition in the periods between milkings. A significant loss of the composition would be a loss whereby the composition would no longer have its protective properties.

Since the polyurethane is a preformed polymer having no reactive isocyanate groups, it is stable in solution for indefinite periods of time. Accordingly, polymer products of the instant invention can be readily formed at the point of application as needed simply by evaporating any solvent(s) with which they may be associated. This versatility makes the instant products especially convenient for use as coatings.

The composition can be applied to the dairy animal in a variety of ways. The material can be sprayed, brushed, dabbed, or flooded onto the susceptible sites. One common application mode is by means of a dip. The compositon is placed in a small container with a shape adapted to the teat. The teat is then dipped into the container filled with the aqueous composition.

The composition may contain various viscosity enhancers or thickeners. The thickener causes aqueous compositions to cling to the surface skin of the animal and enables the composition to resist waste through excessive dripping. Thus, the composition remains in place until it is dry and the barrier layer is formed. In its preferred embodiment, the viscosity of the composition ranges from about 1–1500 cP. This range in viscosity allows an adequate amount of the composition to remain on the mammalian teat when applied without being overly viscous which would make application difficult by dipping or other methods. Thickeners which may be used in the present invention include natural gums such as xanthan gum (Keltrol TF, Keltrol).

After the mammalian teats have been coated with the composition of this invention, the resulting coating is permitted to dry to an adherent solid film on the teats. Typically, some of the still liquid coating material flows down to the teat end where a plug-like deposit is formed. This deposit or plug also dries to form an adherent solid. This plug is capable of sealing off the teat canal.

The protective barrier formed on the mammalian skin is a residual, elastic film, that is water-resistant, when applied to these skin surfaces. The film is flexible, long-lived and resists cracking. The film contains the antimicrobial material that kills microorganisms on the skin surface. Such antimicrobial action is important because the milking operation can often spread mastitis causing microorganisms which can under certain circumstances cause inflammation and infection in abraded or affected skin resulting from contact with milking machines during milking operations. Additionally, the barrier film also protects the mammalian skin from mastitis-causing organisms between milkings. The films of this invention are highly water-resistant. They can remain on the mammal for up to eight hours despite exposure of the animal to environmental water such as rain, dew, ponds, mud, etc. In contrast, polyvinyl alcohol-based formulations wear off in about three to four hours.

Surprisingly, despite the highly water-resistant feature of this composition, the film and the plug are removable without tedious physical steps. The composition can be easily removed by washing with a mild surfactant and wiping with a cloth. The composition may even be removed with warm water alone and more extended wiping.

The composition can also contain water-soluble or water-dispersible skin conditioning or moisturizing agents which do not degrade barrier properties. The preferred range of these agents in the composition is 0.05% to 10%. Examples of these ingredients are glycerin; glycols; polyols, such as polyethylene glycol; lanolin; aloe vera and vitamins, such as E, C and A. These agents serve to assist in soothing and retaining moisture on the skin.

Agents such as colorants, fragrances and insect repellants (e.g., citronella) may also be included in the composition.

Buffering agents utilized in this invention include the acid form and base salt of an organic or inorganic acid in such a ratio to produce a resultant pH value for the finished composition from about 4 to 6.5.

The following examples are illustrative of the composition of this invention and provide a best mode.

EXAMPLES OF THE INVENTION

EXAMPLE 1

To 89.5 grams of water was added 0.5 grams of xanthan gum (Keltrol TF, Keltrol) with stirring. The solution was mixed until homogeneous. Then 5.0 grams of a hydrophilic polymer blend as taught by U.S. Pat. No. 4,642,267 (Hydromer, Inc.) was added with stirring until homogeneous. Next, 5.0 grams of an aqueous iodine solution (AST Inc.) was added and the solution was mixed until well blended. The solution was buffered with sodium bicarbonate to bring to a pH of approximately 5.5. The solution has a typical iodine color. The solution does not drip when cast onto a plate and held vertically, and films cast from the resulting solution are elastic and water-resistant which prevents the spread of mastitis causing organisms.

EXAMPLE 2

To 86.7 grams of water was added 1.4 grams of citric acid (Fischer Chemical Company) with stirring. Once dissolved, approximately 2 grams of sodium bicarbonate was added to bring the pH to approximately 5.5. Next, 0.5 grams xanthan gum (Keltrol CGT, Keltrol) was added with stirring. The solution was mixed until homogeneous. Then 5.0 grams of a hydrophilic polymer blend as taught by U.S. Pat. No. 4,642,267 (Hydromer, Inc.) was added with stirring until homogeneous. Next, 5.0 grams of an aqueous iodine solution (AST Inc.) was added and the solution was mixed until well blended. The solution has a typical iodine color. The solution of pH approximately 5.5 does not drip when cast onto a plate and held vertically, and films cast from the resulting solution are elastic and water resistant which prevents the spread of mastitis causing organisms.

EXAMPLE 3

To 90.4 grams of water was added 1.4 grams of citric acid (Fisher Chemical Company) with stirring. Once dissolved, approximately 2 grams of sodium bicarbonate was added to bring the pH to approximately 5.5. Next, 0.1 grams xanthan gum (Keltrol CGT, Keltrol) was added with stirring. The solution was mixed until homogeneous. Then 5.0 grams of a hydrophilic polymer blend as taught by U.S. Pat. No. 4,642,267 (Hydromer Inc.) was added with stirring until homogenous. Next, 5.0 grams of an aqueous iodine solution (AST Inc.) was added and the solution was mixed until well blended. The solution has a typical iodine color. A solution of pH approximately 5.5 does not drip when sprayed on a plate and held vertically, and films cast from the resulting solution are elastic and water resistant which prevents the spread of mastitis causing organisms.

EXAMPLE 4

To 94.3 grams of water was added 0.5 grams of xanthan gum (Keltrol CGT, Keltrol) with stirring. The solution was mixed until homogeneous, then 5.0 grams of a hydrophilic polymer blend as taught by U.S. Pat. No. 4,642,267 (Hydromer Inc.) with stirring until homogeneous. Next, 0.2 grams bronopol (Inolex Chemical) was added and the solution mixed until well blended. The solution was buffered with sodium bicarbonate to bring to a pH of approximately 5.5. The solution has a typical iodine color. The solution does not drip when cast onto a plate and held vertically, and films cast from the resulting solution are elastic and water resistant which prevents the spread of mastitis causing organisms.

EXAMPLE 5

To 91.9 grams of water was added 0.1 grams of poly (ethylene oxide) (Americhol) with stirring. The solution was mixed until homogeneous, then 5.0 grams of a hydrophilic polymer blend, as taught by U.S. Pat. No. 4,642,267 (Hydromer Inc.),was added with stirring until homogeneous. Next, 3.0 grams of an aqueous chlorhexidene gluconate solution was added and mixed until well blended. The solution was buffered with sodium bicarbonate to bring to a pH of approximately 5.5. The solution has a typical iodine color. The solution does not drip when sprayed onto a plate and held vertically, and films cast from the resulting solution are elastic and water-resistant which prevents the spread of mastitis causing organisms.

EXAMPLE 6

To 94.0 grams of water was added 0.5 grams of xanthan gum (Keltrol CGT, Keltrol) with stirring. The solution was mixed until homogeneous. Then 5.0 grams of a hydrophilic polymer blend, as taught by U.S. Pat. No. 4,642,267 (Hydromer Inc.), was added with stirring until homogeneous. Next, 0.5 grams of triclosan (Ciba Speciality Chemicals) was added and the solution was mixed until dispersed. The solution was buffered with sodium bicarbonate to bring to a pH of approximately 5.5. The solution has a typical iodine color. The solution does not drip when cast onto a plate and held vertically, and films cast from the resulting solution are elastic and water resistant which prevents the spread of mastitis causing organisms

EXAMPLE 7

To 86.7 grams of water was added 1.4 grams of citric acid (Fisher Chemical Company) with stirring. Once dissolved, approximately 2 grams of sodium bicarbonate was added to bring the pH to approximately 5.5. Next, 0.5 grams of xanthan gum (Keltrol CGT, Keltrol) was added with stirring. The solution was mixed until homogeneous. Then 5.0 grams of a hydrophilic polymer blend as taught by U.S. Pat. No. 4,642,267 (Hydromer, Inc.) was added with stirring until homogeneous. Next, 5.0 grams of an aqueous iodine solution (AST Inc.) was added and the solution was mixed until well blended. A solution of pH approximately 5.5 does not drip when cast onto a plate and held vertically, and films cast from the resulting solution are elastic and water resistant which prevents the spread of mastitis causing organisms.

EXAMPLE 8

To 74.7 grams of water was added 1.4 grams of citric acid (Fischer Chemical Company) with stirring. Once dissolved, approximately 2 grams of sodium bicarbonate was added to bring the pH to approximately 5.5. Next, 0.5 grams xanthan gum (Keltrol CGT, Keltrol) was added with stirring. The solution was mixed until homogeneous. Then 5.0 grams of a hydrophilic polymer blend as taught by U.S. Pat. No. 4,642,267 (Hydromer, Inc.) was added with stirring until homogeneous. Next, 17.0 grams of PVP-$I_2$ were added and the solution was mixed until well blended. A solution of pH approximately 5.5 does not drip when cast onto a plate and held vertically, and films cast from the resulting solution are elastic and water resistant which prevents the spread of mastitis causing organisms.

EXAMPLE 9

To 86.2 grams of water was added 1.4 grams of citric acid (Fischer Chemical Company) with stirring. Once dissolved, approximately 2 grams of sodium bicarbonate was added to bring the pH to approximately 5.5. Next, 0.5 grams of xanthan gum (Keltrol CGT, Keltrol) was added with stirring. The solution was mixed until homogeneous. Then 5.0 grams of a hydrophilic polymer blend as taught by U.S. Pat. No. 4,642,267 (Hydromer, Inc.) was added with stirring until homogenous. Next, 5.0 grams of an aqueous iodine solution (AST Inc.) was added and the solution was mixed until well blended. Finally, 0.5 grams of aloe vera (Terry Labs) was added and mixed until homogeneous. A solution of pH approximately 5.5 does not drip when cast onto a plate and held vertically, and films cast from the resulting solution are elastic and water resistant which prevents the spread of mastitis causing organisms.

EXAMPLE 10

To 81.7 grams of water was added 1.4 grams of citric acid (Fischer Chemical Company) with stirring. Once dissolved, approximately 2 grams of sodium bicarbonate were added to bring the pH to approximately 5.5. Next, 0.5 grams of xanthan gum (Keltrol CGT, Keltrol) was added with stirring. The solution was mixed until homogeneous. Then 5.0 grams of a hydrophilic polymer blend as taught by U.S. Pat. No. 4,642,267 (Hydromer, Inc.) were added with stirring until homogenous. Next, 5.0 grams of an aqueous iodine solution (AST Inc.) were added and the solution was mixed until well blended. Finally, 0.5 grams of glycerin (Aldrich Chemical) were added and the solution mixed until homogeneous. A solution of pH approximately 5.5 does not drip when cast onto a plate and held vertically, and films cast from the resulting solution are elastic and water resistant which prevents the spread of mastitis causing organisms.

While the present invention has been described with reference to specific embodiments thereof, it should be understood by those skilled in this art that various changes may be made and equivalents may be substituted without departing from the true spirit and scope of the invention. In addition, many modifications can be made to adapt a particular situation, material or composition of matter, process, process step or steps, or then-present objective to the spirit of this invention without departing from its essential teachings.

EXAMPLE 11

Antimicrobial Properties

Fresh cultures of *E. coli* ATCC 11229 and *Staph. aureus* ATCC 6538 and Strep. Agalactiae ATCC 13813, prepared from cultures maintained in the microbiology stock culture maintenance program at a concentration of approximately $10 \times 10^9$, were added separately to vials containing 100 ml of the mammalian teat dip. The final concentration of organisms in each vial was approximately $10^7$ per ml. At exactly 30 and 60 seconds after addition of each inoculum, a 1 ml portion was removed from each vial and pipetted into a 99 ml sterile phosphate buffered saline (PBS) dilution blank. Each organism concentration was then enumerated from 99 ml dilution blank using serial dilution and agar pour plate technique. A negative control (initial numbers control) using a 100 ml PBS was employed to verify the initial inoculum of each organism. Results of each recovered organism were reported in colony forming units (CFU) per ml of product.

Results of the study indicate a >6.0 log reduction for all organisms within 30 seconds after exposure to the tested materials.

| *E. coli* ATCC #11229 $1.9 \times 10^7$ CFU/ml challenge | | | |
|---|---|---|---|
| Test Substance | Time exposure | Challenge *E coli* CFU/ml | Log Reduction |
| Solution in Example #1 | 30 seconds | $1.9 \times 10^7$ | >6.0 |
| Solution in Example #1 | 30 seconds | $1.9 \times 10^7$ | >6.0 |
| Solution in Example #1 | 60 seconds | $1.9 \times 10^7$ | >6.0 |
| Solution in Example #1 | 60 seconds | $1.9 \times 10^7$ | >6.0 |

| *Staph Aureus* ATCC # 6538 $1.2 \times 10^7$ CFU/ml challenge | | | |
|---|---|---|---|
| Test Substance | Time exposure | Challenge *S. aureus* CFU/ml | Log reduction |
| Solution in Example #1 | 30 seconds | $1.2 \times 10^7$ | >6.0 |
| Solution in Example #1 | 30 seconds | $1.2 \times 10^7$ | >6.0 |
| Solution in Example #1 | 60 seconds | $1.2 \times 10^7$ | >6.0 |
| Solution in Example #1 | 60 seconds | $1.2 \times 10^7$ | >6.0 |

| *Strep. Agalactiae* ATCC 13813 $2 \times 10^7$ CFU/ml challenge | | | |
|---|---|---|---|
| Test Substance | Time exposure | Challenge *S. agalactiae* CFU/ml | Log reduction |
| Solution in Example #1 | 30 seconds | $2 \times 10^7$ | >6.0 |
| Solution in Example #1 | 30 seconds | $2 \times 10^7$ | >6.0 |
| Solution in Example #1 | 60 seconds | $2 \times 10^7$ | >6.0 |
| Solution in Example #1 | 60 seconds | $2 \times 10^7$ | >6.0 |

EXAMPLE 12

Test of the Microbial Barrier Properties of the Mammalian Teat Dip Composition

Prepartion of *B. diminuta* suspension:

A cryovial of prepared cell paste was briefly placed into 80% ethanol. Next the vial was flamed to remove residual ethanol. Using sterile forceps, the cap was removed from the vial and the cell paste was placed into a sterile jar with 19 ml 0.9% saline. The suspension was mixed for 30–40 minutes prior to use. Plate counts were performed on the suspension to determine CFU/ml. The prepared stock suspension was adjusted to yield $10^6$–$10^7$ CFU/ml.

Testing Procedure:

1. A test apparatus was prepared by removing the 0.22 $\mu$m filter from a Nalgene filter apparatus with a sterile scalpel.
2. A Millipore stainless steel 100-micron screen was placed inside the test apparatus.
3. Approximately 2 ml of the mammalian teat dip composition of the present invention was placed onto the screen in the test apparatus. The composition was allowed to solidify for four hours, making sure the screen was completely covered prior to drying.
4. One hundred ml of sterile TSB (trisodium buffer) was aseptically added to the Nalgene collection container of the test apparatus.
5. The composition in the test apparatus was sprayed with a $10^6$–$10^7$ CFU/ml suspension of *B. diminuta* using a tester's airbrush for 10 seconds at 30 PSI pressure.

6. The test apparatus was removed and the collection container was capped with the sterile cap provided. All the steps were repeated for two other samples of the composition.
7. The collection containers were incubated at 32–35° C. for seven days.
8. Steps 4 through 7 were performed using a test apparatus without the composition (positive control) and using a test apparatus in which the 0.22 μm filter was not removed (negative control).
9. The samples are considered to pass the test if no growth was observed in the samples after 7 days of incubation. The negative and positive controls must be satisfactory or the test is invalid.

All three samples of the composition of the present invention passed the Microbial Barrier Test. No growth was observed in the samples after seven (7) days of incubation. Controls were satisfactory.

What is claimed is:

1. A mammalian teat dip composition comprising:
   (i) a solution of a film forming polymer blend comprising a first polymer component which is an organic, solvent-soluble, preformed, thermoplastic polyurethane having no reactive isocyanate groups and a second polymer component which is a hydrophilic poly(N-vinyl lactam), said blend capable of withstanding exposure to water without significant loss of said hydrophilic poly(N-vinyl lactam) in an amount sufficient to form a water-resistant film upon topical application to mammalian skin; wherein said blend comprises from about 10 to about 80 weight percent of said first polymer and from about 20 to about 90 weight percent of said second polymer;
   (ii) at least one antimicrobial agent in an amount sufficient to treat and protect mammalian skin from infection; and
   (iii) sodium bicarbonate in amount to provide said composition with a pH of approximately 4 to 6.5;
   wherein said composition is capable of being removed easily from said mammalian skin with a surfactant and water.

2. A composition according to claim 1 wherein said antimicrobial agent is selected from the group consisting of iodine, chlorhexidine, bronopol and triclosan.

3. A composition according to claim 2 wherein said antimicrobial agent is an aqueous solution of iodine which comprises 50% to 80% by weight of water and 20% to 50% by weight of polyvinylpyrrolidone-iodine.

4. A composition according to claim 2 wherein said antimicrobial agent is an aqueous solution of iodine which comprises 50% to 98.9% by weight of water, 0.1% to 49% by weight of elemental iodine, and 1% to 49.9% by weight of iodide salts.

5. A composition according to claim 2 wherein said antimicrobial agent is an aqueous solution of iodine which comprises 50% to 97.9% by weight of water, 0.1% to 48% by weight of elemental iodine, 1% to 48.9% by weight of hydriodic acid, and 1% to 48.9% by weight of a surfactant.

6. A composition according to claim 1 wherein the poly(N-vinyl lactam) is a water-soluble polyvinylpyrrolidone homopolymer; or is a poly(N-vinyl caprolactam) homopolymer.

7. A composition according to claim 2 wherein said antimicrobial agent is an aqueous solution of chlorhexidine which comprises 50% to 99% by weight of water and 1.0% to 50% by weight of chlorhexidine salts.

8. A composition according to claim 1 wherein said polyurethane is derived from an aromatic polyisocyanate and a polyether polyol; or is derived from an aliphatic polyisocyanate and a polyether polyol; or is derived from an aromatic polyisocyanate and a polyester polyol; or is derived from an aliphatic polyisocyanate and a polyester polyol.

9. A composition according claim 1 containing at least one additional polymer component which is compatible therewith.

10. A composition according to claim 9 wherein said additional polymer component is a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

11. The composition according to claim 1 further including at least one agent selected from the group consisting of skin conditioning agents, colorants, fragrances and insect repellants.

12. The composition according to claim 11 wherein said skin conditioning agent is selected from the group consisting of glycerin, glycols, polyols, lanolin, aloe vera and vitamins.

13. A method of protecting mammalian teat from infection comprising:
   (i) applying to mammalian teat a composition comprising a solution of a film forming polymer blend comprising a first polymer component which is an organic, solvent-soluble, preformed, thermoplastic polyurethane having no reactive isocyanate groups, a second polymer component which is a hydrophilic poly(N-vinyl lactam) and sodium bicarbonate in amount to provide said composition with a pH of approximately 4 to 6.5, said blend capable of withstanding exposure to water without significant loss of said hydrophilic poly(N-vinyl lactam), in an amount sufficient to form a water-resistant film upon application to mammalian skin; and an antimicrobial agent in an amount sufficient to treat and protect mammalian skin from infection; wherein said blend comprises from about 10 to about 80 weight percent of said first polymer and from about 20 to about 90 weight percent of said second polymer; and
   (ii) evaporating solvent of said solution whereby a protective water resistant film is formed on said mammalian teat.

14. A protective film disposed on mammalian teat comprising:
   (i) a solution of a film forming polymer blend comprising a first polymer component which is an organic, solvent-soluble, preformed, thermoplastic polyurethane having no reactive isocyanate groups, a second polymer component which is a hydrophilic poly(N-vinyl lactam) and sodium bicarbonate in amount to provide said composition with a pH of approximately 4 to 6.5, said blend capable of withstanding exposure to water without significant loss of said hydrophilic poly(N-vinyl lactam), in an amount sufficient to form a water-resistant film upon topical application to mammalian skin; wherein said blend comprises from about 10 to about 80 weight percent of said first polymer and from about 20 to about 90 weight percent of said second polymer; and
   (ii) an antimicrobial agent in an amount sufficient to treat and protect mammalian skin from infection.

15. A method according claim 13 wherein said antimicrobial agent is selected from the group consisting of iodine, chlorhexidine bronopol and triclosan.

16. A method according to claim 13 wherein said antimicrobial agent is an aqueous solution of iodine which comprises 50% to 80% by weight of water and 20% to 50% by weight of polyvinylpyrrolidone-iodine; or 50% to 98.9% by weight of water, 0.1% to 49% by weight of elemental iodine, and 1% to 49.9% by weight of iodide salts; or 50% to 97.9% by weight of water, 0.1% to 48% by weight of elemental iodine, 1% to 48.9% by weight of hydriodic acid, and 1% to 48.9% by weight of a surfactant.

17. A method according to claim 13 wherein said antimicrobial agent is an aqueous solution of chlorhexidine which comprises 50% to 99% by weight of water and 1.0 to 50% by weight of chlorhexidine salts.

18. A method according to claim 13 wherein said polyurethane is derived from an aromatic polyisocyanate and a polyether polyol; or is derived from an aliphatic polyisocyanate and a polyether polyol; or is derived from an aromatic polyisocyanate and a polyester polyol; or is derived from an aliphatic polyisocyanate and a polyester polyol.

19. A method according to claim 13 wherein the poly(N-vinyl lactam) is a water-soluble polyvinylpyrrolidone homopolymer; or is a poly(N-vinyl caprolactam) homopolymer.

20. A method according claim 13 containing at least one additional polymer component which is compatible therewith.

21. A method according to claim 20 wherein said additional polymer component is a homopolymer or copolymer of at least one monomer selected from the group consisting of alpha-olefin, vinyl chloride, vinylidene chloride, hydroxyethylmethacrylate, acrylic acid, methacrylic acid, vinyl acetate, vinyl alcohol, and vinyl ether.

22. A method according to claim 13 further including at least one agent selected from the group consisting of skin conditioning agents, colorants, fragrances and insect repellants.

23. A method according to claim 22 wherein said skin conditioning agent is selected from the group consisting of glycerin, glycols, polyols, lanolin, aloe vera and vitamins.

* * * * *